United States Patent [19]

Green et al.

[11] Patent Number: 5,139,933

[45] Date of Patent: Aug. 18, 1992

[54] ASSAY METHOD FOR DETECTING LISTERIA

[75] Inventors: Calvert L. Green, Norfolk, Mass.; Franz Fiedler, Munich, Fed. Rep. of Germany; Thomsen J. Hansen, Brookline; Gerald N. Wogan, Belmont, Mass.; Steven R. Tannenbaum, Framingham, Mass.; Thomas L. Benjamin, Cambridge, Mass.

[73] Assignee: VICAM, L.P., Somerville, Mass.

[21] Appl. No.: 542,695

[22] Filed: Jun. 25, 1990

Related U.S. Application Data

[63] Continuation-in-part of Ser. No. 459,246, Dec. 29, 1989, abandoned, which is a continuation-in-part of Ser. No. 412,446, Sep. 26, 1989, abandoned.

[51] Int. Cl.$^5$ .......................................... G01N 33/569
[52] U.S. Cl. .................. 435/732; 435/7.92; 435/29; 435/961; 435/176; 435/820; 436/526; 436/532
[58] Field of Search .............. 435/7.32, 7.8, 7.9, 435/7.92, 7.94, 7.95, 820, 803, 964, 962, 961, 174, 176, 181; 436/518, 524, 525, 526, 528, 529, 530, 531, 534, 547, 548

[56] References Cited

U.S. PATENT DOCUMENTS

| | | | |
|---|---|---|---|
| 4,230,685 | 10/1980 | Senyei et al. | 436/526 |
| 4,231,999 | 11/1980 | Carlsson et al. | 435/7.8 |
| 4,596,769 | 6/1986 | Shockman et al. | 435/7.32 |
| 4,950,589 | 8/1990 | Butman et al. | 435/7.32 |

OTHER PUBLICATIONS

Fiedler et al., Syst. Appl. Microbiol. 5(3), 360-376 (1984).
Bergey's Manual of Systematic Bacteriology, Sneath et al, eds. vol. 2, p. 1242 (1986).
American Type Culture Collection Catalogue of Bacteria and Phayes, 17th Ed., p. 124 (1989).
Ngo et al, Enzyme-Medicated Immunossay p. 283 (1985).
Mattiasson et al "Ch. 11 Novel Approaches to Enzyme-Immunoassay", Enzyme-Immunoassay, Maggio, Editer, pp. 224-227 (1980).
Kamisango et al. "Enzyme Immunoassay of Teichoic Acids from Listeria monocytogenes" J. Chim. Microbiol, (Jun. 1985), 21(1) 135-137.
Kaya et al, "Characterization of a novel linkage unit between ribitol teichoic acid and peptidoglycan in Listeria monocytogenes cell walls", Eur. J. Biochem. 146:517-522 (1985).
De Cueninck et al, "Group B, Type III Streptococcal Cell Wall", Infect. Immun. 35(2), 572-582 (Feb. 1982).
Sutherland, "Chapter 2 Separation and purification of bacterial antigens" Handbook of Experimental Immunology, 3rd Ed. pp. 2.1-2.17 (1978).
Voller et al, "Chapter 17 Enzyme-Linked Immunosorbent Assay" in Manual of Clinical Laboratory Immunology, 3rd Ed. pp. 99-109 (1986).

Primary Examiner—Esther L. Kepplinger
Assistant Examiner—Carol E. Bidwell
Attorney, Agent, or Firm—Birch, Stewart, Kolasch & Birch

[57] ABSTRACT

An assay method is provided to quickly detect the presence of Listeria strains in samples, characterized by the use of antibodies to selectively capture the peptidoglycan and teichoic acid components of the listeriae bacterial cell wall.

25 Claims, 5 Drawing Sheets

Peptidoglycan  Protein

Lipoteichoic acid

CW Cell wall

Teichoic acid

CM Cell membrane

Gro: glycerol
ManNAc: N-acetylmannosaminyl
MurNAc: N-acetylmuramyl

ASSAY METHOD FOR DETECTING LISTERIA

CROSS-REFERENCE TO RELATED APPLICATIONS

This is a continuation-in-part of application Ser. No. 07/459,246 filed on Dec. 29, 1989, now abandoned, which is in turn a continuation-in-part of application Ser. No. 07/412,446 filed on Sep. 26, 1989, now abandoned.

FIELD OF THE INVENTION

This invention relates to an assay method for quickly and easily detecting the presence of Listeria bacteria. In particular, an immunoassay method is utilized to detect the presence of Listeria strains in foods and other potentially contaminated samples using an assay characterized by the combined use of antibodies specific for two separate cell wall components, namely peptidoglycan and teichoic acids.

BACKGROUND OF THE INVENTION

The presence of bacterial pathogens is a well recognized cause of various medical and etiological problems, so that there is an ever present need for the detection of bacterial pathogens in both clinical specimens (i.e. blood, tissue, urine and other body extracts and fluids) and agricultural specimens (such as food products).

However, current tests for the detection of bacterial pathogens, such as in food, typically require a number of days to complete. During this period of time, between sampling and assay determination, fresh food and dairy products will enter the food chain and therefore be consumed by the public. If a test indicates the presence of pathogens, expensive product recalls may result, or, worse, before the test results are discovered an outbreak of sickness may occur.

This was exactly the case in a number of recent outbreaks of Listeria in fresh dairy and vegetable products. In the case of Listeria, an outbreak generally produces a death rate greater than 40%. In addition this rate is much higher for newborns, pregnant women, the elderly and immunocompromised individuals. Spontaneous abortions result even in otherwise asymptomatic patients. In fact, it is estimated that as many as 2% of all spontaneous abortions may be due to Listeria infection.

As stated above, traditional methods to detect the presence of bacterial food pathogens require an extended period of time, basically due to the need for an incubation period. This incubation period is intended to allow for recovery of injured bacteria, growth of these bacteria from a background of competing microorganisms and an increase in bacterial cell numbers to more readily aid in identification. In many cases a series of two or three separate incubations is needed to isolate the target bacteria.

In the standard FDA procedure for detection of Listeria in food products (Bacteriological Analytical Manual, 6th ed., 1984; Supplement, September 1987, Chapter 29) 25 g or 25 ml of a food sample is mixed with 225 ml of enrichment broth. This sample in broth mixture is incubated for 7 days. At the end of days 1 and 7 a sample of the broth culture is streaked onto petri plates containing selective growth agar and these plates are incubated for an additional 2 days. Identification of Listeria colonies confirms the presence of Listeria in the original food sample. This identification, however, is subjective, and therefore prone to misinterpretation, and this procedure requires a minimum of 7 days to confirm Listeria negative samples.

These conventional methods are slow, requiring 5–14 days, or more, depending upon the bacteria species of interest. In a given food sample it is also possible to miss target bacteria (false negatives) due to many reasons including inadequate incubation conditions (time, growth media), subjectivity of the person interpreting the results, identification on petri plates, over-growth by competing organisms or a combination of these and other problems.

More recent methods of bacterial detection in food products have utilized immunoassays. Antibodies to an antigen present in the bacteria of interest are generally used in these methods in some form of a two site assay. That is, one antibody is immobilized and acts to capture the target bacterial antigens. This allows for separation of the target antigen from the food sample. A second antibody to this antigen (having the same or a different epitope) is labeled in some fashion such as radioactively with $I^{125}$ or enzymatically with horse radish peroxidase, and when added to the immobilized antibody antigen complex is also immobilized. Subsequent steps remove unbound labeled antibody. The label left attached is measured and usually compared against standards (positive and negative controls) to determine the presence of the target bacteria. At least one of the two antibodies used in the two site assay must be specific to the target bacteria. This type of immunoassay is known as a direct assay. Other forms, such as the competition assay are also used but tend to be less sensitive.

Because of the actual sensitivity limit of these assays it remains necessary to culture the target bacteria from the food sample. In some of the newer immunoassay tests incubation times have been reduced and the number of separate incubation steps have also been reduced. The resulting tests, however, still require about 48 hours to complete. Many of the problems associated with culturing the target organisms, as described above, also remain.

In a generalized "rapid" immunoassay for detection of Listeria, 25 g or 25 ml of food sample is mixed with 225 ml of enrichment broth, as in the FDA procedure. This culture mixture is incubated for 24 hours. From this 250 ml of culture, 1 ml is removed and added to 9 ml of selective growth medium. This selective culture mixture is incubated for an additional approximately 24 hours. At this point, depending upon the actual immunoassay format, some fraction of the total 10 ml subculture (usually 0.2 ml–1.0 ml) is tested by immunoassay for the presence of Listeria.

In summary, these existing "rapid" immunoassay procedures for bacterial detection in food samples all require at least one (usually two or more) dilution of sample step (into growth medium) followed by an assay procedure which only utilizes a fraction of this final culture. The actual assay sample thus only corresponds to a small fraction of the original food sample. The bacterial culture step, or steps, must therefore overcome this dilution factor, adding to the amount of needed culture time.

These and other disadvantages of the prior art methods are overcome by the present invention which provides a fast and accurate method for the detection of Listeria.

OBJECTS AND SUMMARY OF THE INVENTION

It is, therefore, one object of the present invention to provide a method for quickly detecting the presence of bacterial pathogens.

It is another object of the invention to provide a method for the detection of Listeria bacteria which requires little or no culturing of the bacterial cells.

It is a further object of the invention to provide a rapid method for the detection of Listeria.

It is a still further object of the invention to quantitate the number of Listeria cells in a sample.

These and other objects of the invention are accomplished by providing a method which selectively removes bacteria from a sample by the use of an antibody, lyses the captured cells to release peptidoglycan-teichoic acid (PEP-TA) complexes of the bacterial cell walls, captures the released complexes by the use of a second antibody, and then detects the presence of the PEP-TA complexes by the use of a labeled antibody which is specific for teichoic acid and can subsequently be detected to indicate the presence of the bacterial pathogen.

DETAILED DESCRIPTION OF THE INVENTION

Figure 1:
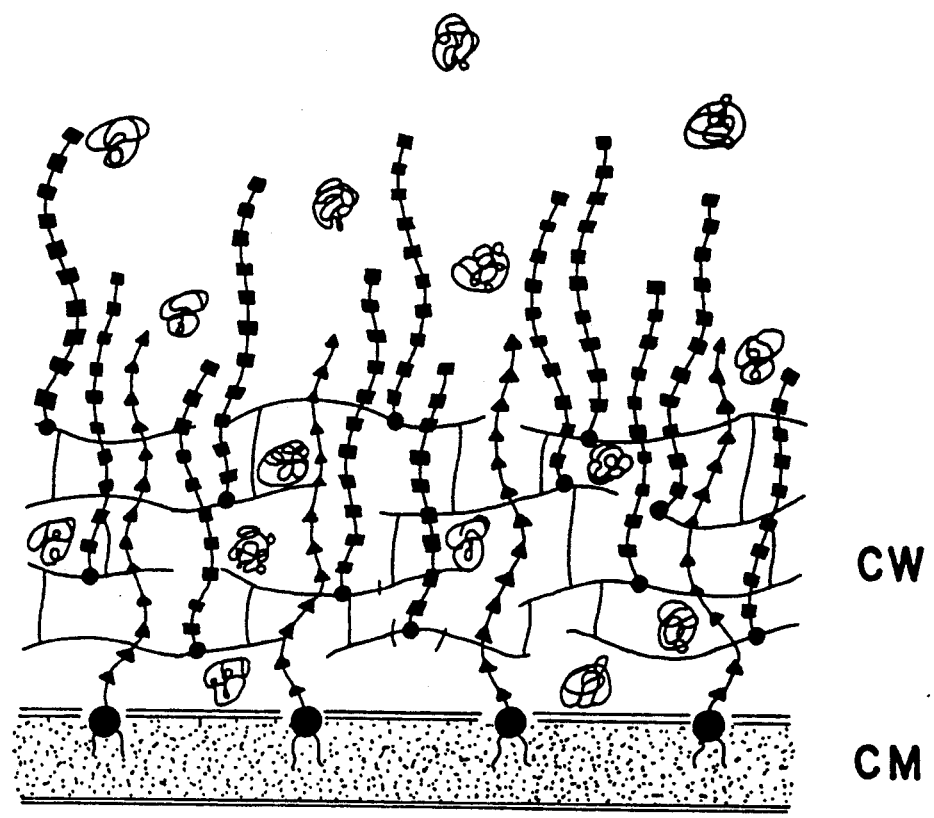
FIG. 1 is a schematic representation of the cell wall of Listeria.
Figure 1:
Figure 1:
Figure 1:
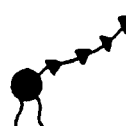
Figure 1:
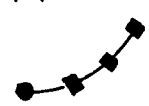

As noted above, one object of the present invention is to provide an immunoassay procedure for rapid identification of Listeria strains in food samples requiring little or no culturing of the bacterial cells. This allows for interpretation of test results prior to release of fresh food products. The present invention overcomes the dilution factor effect by using magnetic bead capture or affinity column technology to concentrate the target bacteria directly from liquid, or liquified food samples. Once concentrated and separated from the food sample, further steps are used to detect the captured bacterial cells. If, for sensitivity of detection, a culturing step is necessary, the addition of a small volume of non-selective growth medium to the separated magnetic beads or directly to the affinity column and a short incubation step will rapidly lead to the increase in cell number necessary for detection for certain bacterial species. The present invention will also allow for a standard incubation step in enrichment broth, followed (without a selective growth step) by the assay procedure as described below.

After the bacteria are immobilized and concentrated according to the invention, the bacteria are treated with cell wall lytic enzymes, or with other methods to in general disrupt cell walls or cellular integrity. The products of this cell wall digestion are then chosen to be the bacterial identification antigens to be selectively identified by antibody assay. The result of releasing these antigens is exposure and accessibility of far more of these target antigens than would be possible utilizing whole bacterial cells as detection targets. Selectivity of the assay is achieved through the specificity of the antibodies used, as well as the means used to release the target antigens from whole bacterial cells.

Another object of the present invention is to increase sensitivity of immunoassays used for bacterial detection. As stated above, one way of doing this is to utilize as many antigenic determinants as possible by making them accessible to the antibodies. Another way to increase sensitivity is to choose antigen targets with the maximum number of antigenic determinants per bacterial cell as possible while still maintaining overall specificity. In the specific example described below, these two aspects of the invention are combined for increased sensitivity.

The method of the invention, therefore, generally comprises the following procedural steps:

1) The sample to be tested for the presence of bacterial pathogens is, if necessary, liquified.

2) The liquified sample is combined with a solid matrix having immobilized thereon monoclonal or polyclonal antibodies to the target bacterial cells. If present the target bacterial cells are thereby immobilized to the solid matrix. The solid matrix with immobilized cells attached is then washed to remove the remainder of the food sample.

3) The immobilized cells (captured by the antibodies) are treated to release target antigens, i.e. peptidoglycan-teichoic acid complexes, from the cell walls.

4) The thus treated complexes are combined, such as by passing through an affinity column, with an affinity matrix having bound thereto antibodies to the peptidoglycan (PEP) moiety, whereby the peptidoglycan moiety is captured by the antibodies.

5) A solution containing labeled antibodies to the teichoic acid (TA) moiety of the PEP-TA complex is combined with the column matrix whereby these labeled antibodies bind to the teichoic acid portion of the captured PEP-TA complexes.

6) The affinity matrix is then treated with a releasing agent to release the label from the matrix, or break any part of the linkage to the matrix; and the presence of labeled monoclonal antibodies is detected as a direct indicator of the presence of the bacterial pathogen.

As can be seen from the above method scheme, the method of the invention is particularly characterized by the use of an antibody to first select out bacteria from a sample, and the use of two additional antibodies which are selective for a particular cell wall component of the selected bacteria. Utilizing these characteristic features, the method of the invention can be importantly applied to the rapid detection of Listeria strains, quantitation of the number of Listeria strain cells in a sample, and (if desired) to selective identification of Listeria strains.

As noted above, one characteristic feature of the method of the invention is the use of the PEP-TA complex as a capture-target antigen group to selectively detect the presence of Listeria strains, taking advantage of the fact that Listeria strains contain a number of differing teichoic acids. The cell wall of Listeria strains is composed of diaminopimelic type peptidoglycan, ribitol containing teichoic acid, lipoteichoic acid and protein. The general organization of these cell wall components was described by Fiedler, F. (1988) in Infection 16, Suppl. 2, pp. 392-397 and is shown in FIG. 1.

Figure 2:
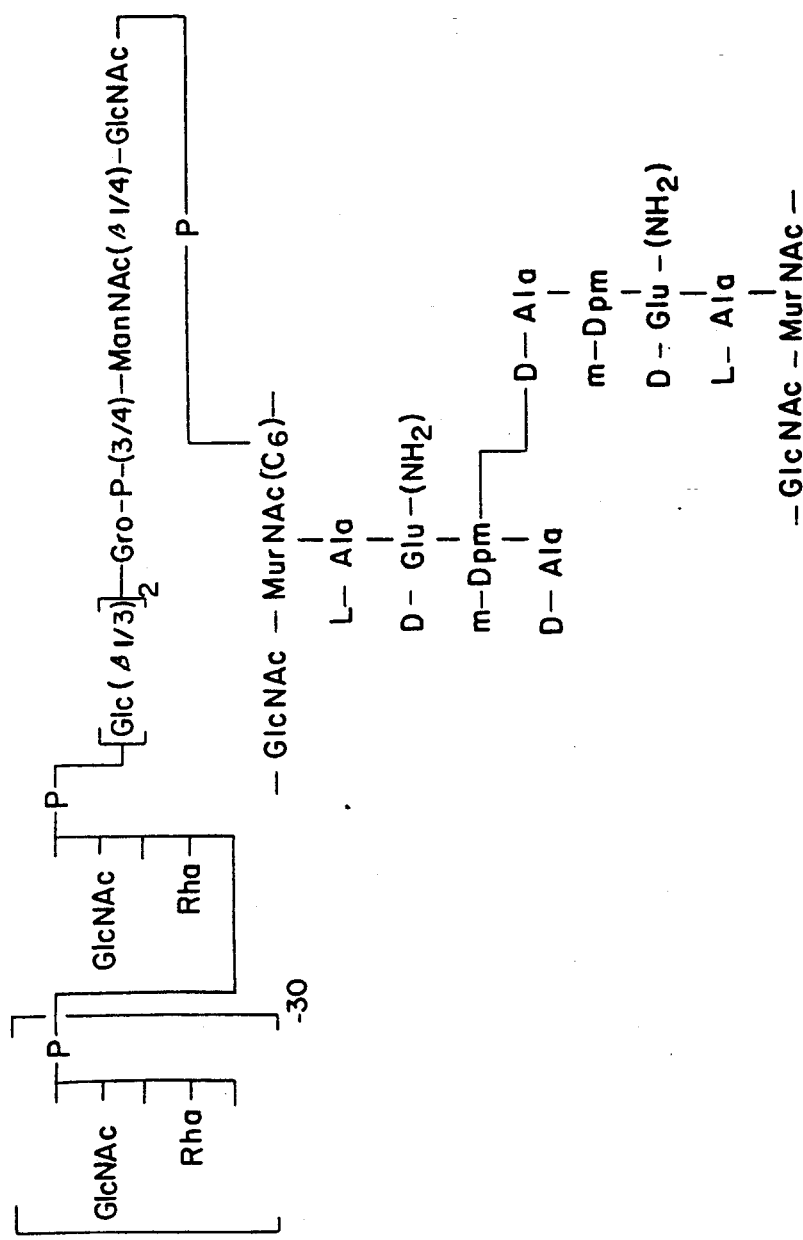
FIG. 2 shows the chemical structure of a position of the peptidoglycan matrix.

As can be seen in FIG. 1, the cell wall includes a peptidoglycan matrix to which are bound a large number of teichoic acid molecules. An example of the chemical structure of a portion of the peptidoglycan matrix covalently attached to an individual teichoic acid molecule in one Listeria strain is shown in FIG. 2. The teichoic acid molecule includes a sugar moiety comprised of ribitol or a substituted ribitol. In a single teichoic acid molecule, an individual ribitol or substituted ribitol is repeated approximately 30 times. In addition, there are differences in the sugar substitution to the ribitols in different strains of Listeria. These differences in the ribitol substitution among strains of Listeria are shown in FIG. 3.

The present invention takes advantage of these structural characteristics of the listeriae bacterial cell wall to provide an assay method which is capable of detecting the presence of Listeria strains, and, if desired, is able to distinguish between strains of Listeria. Since only some Listeria strains are known to be pathogenic it is possible to detect only the pathogenic strains, utilizing to advantage the characteristic teichoic acid structure of those strains.

Figure 3:
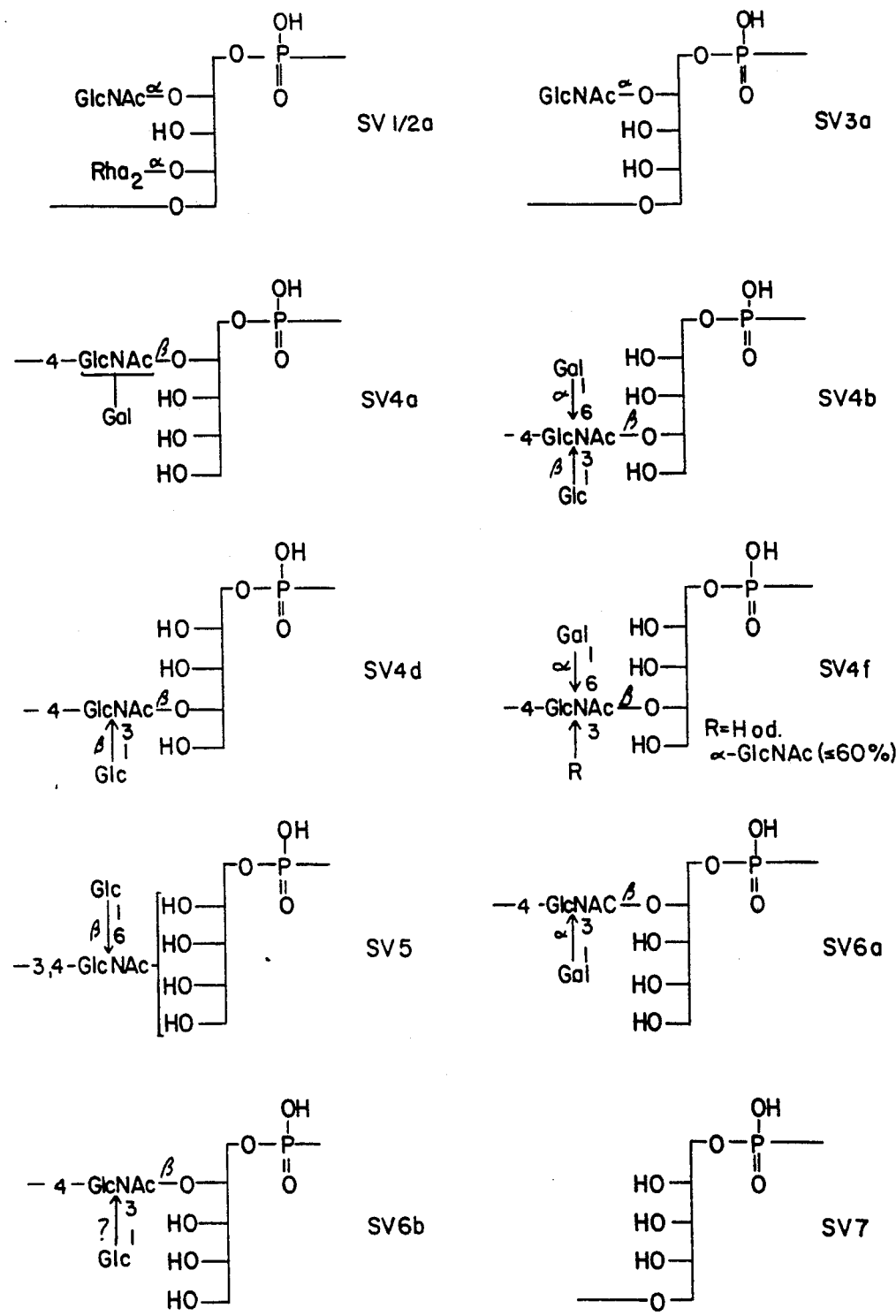
FIG. 3 shows ribitol substitutions among Listeria strains.

In particular, with reference to FIG. 3 showing the ribitol substitutions for different Listeria strains, strains SV 1/2a and 4b are the most common pathogenic strains; SV 5 is primarily an animal pathogen, and the remaining strains are rarely pathogenic.

Detection and selection of the bacteria and cell wall components is accomplished by the use of antibodies. Either polyclonal antibodies or monoclonal antibodies can be used in the individual steps of the assay, depending upon various factors, including the degree of sensitivity desired. If polyclonal antibodies are to be used, then such antibodies can be prepared according to per se known procedures. For example, procedures such as those described by Hurn, B. A. et al. (1980) in Meth. in Enzymology, Ed. Van Vurakis, H. and Langone, J., pp. 104-142, can be used.

The preparation of monoclonal antibodies is known and the monoclonal antibodies used in this invention are prepared using the method originally authored by Milstein and Kohler and published in Nature (1975), 256, pps. 495-497. The basic process involves injecting an animal, usually a mouse, with an immunogenic substance. After suitable time for antibody production to the immunogen, the mouse is sacrificed. Cells are removed from the spleen and fused with myeloma cells. Hybridoma cells resulting from this fusion are able to reproduce in vitro, and each expresses genetic information for one specific antibody. The antibodies produced from one hybridoma fusion thus will only recognize a single antigenic determinant of the immunogen.

Cells cultured from individual hybridoma cells are screened for production of antibodies to the target antigenic determinant. Those hybridomas positive for the target antigen are further screened to identify those having the highest affinity. The monoclonal antibodies used in the present invention will have an affinity of at least $10^8$ liters/mole. Monoclonal antibodies displaying all of these characteristics are then screened using actual assay conditions to determine if the assay condition alters the antibody binding characteristics or affinity, and to screen out those with cross reactivity to possible contaminating antigens.

In the assay method of the invention, three different antibodies are utilized to provide the specific selection and detection desired: (1) an antibody directed to Listeria cells; (2) an antibody directed to the peptidoglycan component of the cell walls; and (3) an antibody directed to the teichoic acid component of the cell walls.

Monoclonal antibodies directed against Listeria cell surface antigens are made by first culturing cells. Attenuated extracts of these cells are then used to immunize mice and the standard procedure for hybridoma production and monoclonal antibody cloning and screening is followed as described above.

Monoclonal antibodies directed against Listeria cell wall teichoic acids are also produced by methods familiar to those in the field. Immunization is carried out using Listeria cell wall preparations made by the method of Schleifer, K. H. and Kandler, O.; (1967) Arch. Mikrobiol. 57, 35-363. These cell wall preparations contain (TA) covalently linked to the cell wall peptidoglycan matrix. For immunization the peptidoglycan will act as the immunogenic carrier. Greater antibody specificity may be achieved by using purified (TA) as the immunizing agent. For this, the cell walls may be digested chemically (for example with 10 mM glycine hydrochloride buffer pH 2.5). The (TA) is then purified and used as the immunogen. To increase the immune response these purified (TA) may be coupled to an immunogenic carrier protein. For example, the reducing sugar end-group of the digested (TA), as above, may be coupled to a carrier protein by reductive amination using the method of Roy et al. (1984) *Canadian J. of Biochem.*, 62, 270-275, as applied to Listeria (TA) by Kamisango et al. (1985), *J. Clin. Microbiol.*, 21, 135-137. In this procedure (TA) are reacted with a carrier protein such as BSA in the presence of sodium cyanoborohydride. The result is a covalent teichoic acid-protein complex which is used for immunization.

Monoclonal antibodies directed against cell wall peptidoglycan (PEP) are made by preparing cell walls as above. Treatment of the cell walls with 10 mM glycine hydrochloride buffer, pH 2.5, followed by centrifugation results in the separation of (TA) into the supernatant and insoluble (PEP) in the pellet. This pellet is resuspended and used as the immunogen. Also possible is further purification of the (PEP) by HPLC or electrophoresis, and the use of purified cleavage fragments from the (PEP) matrix. Using fragments of (PEP) as immunogens was demonstrated by Wergeland, H. I., et al. (1987) J. of Immunol. Meth., 104, 57-63.

Monoclonal antibodies to the cell wall peptidoglycan can also be prepared according to the procedure described in U.S. Pat. No. 4,596,769 to Shockman et al.

The thus prepared monoclonal antibodies are utilized according to the invention in an assay to selectively capture Listeria cells from a sample to be tested, and then to selectively identify the presence of one or more strains of Listeria utilizing the characteristic teichoic acid structures of the individual strains. The assay can be performed according to various types of assay procedures. In particular, the preferred methods of capturing the Listeria cells and Listeria antigens are by magnetic bead capture or affinity column chromatography. However, any other method able to utilize the immobilized antibodies to capture and concentrate the cells and released target antigens is feasible. This would include the use of suspended beads in liquified samples to capture the targets, followed by centrifugation to concentrate the target cells or antigens. Also included is collection of target cells or antigens on sticks or paddles coated with immobilized antibodies and stirred through liquid or liquified samples. In addition methods utilizing filtration of the sample through membranes (listed above) having antibodies attached is included.

The preferred immobilizing matricies for the capturing antibodies are magnetic beads or polyacrylamide beads. However, any other matrix for immobilizing antibodies is feasible. These include beads of agarose or other polysaccharides, cross-linked dextrans, glass beads, latex beads, glass fiber filters, cellulose nitrate filters and nylon filters. Methods to bind antibodies to polyacrylamide beads and other matrices are well known to those in the profession. Carbodiimides may be used to couple antibodies to polyacrylamide beads as described by Bauminger, J., and Wilchek, M. 1980, Methods of Enzymology, 70, 151–159. Another example is a method for generally binding biopolymers to polysaccharides, U.S. Pat. No. 3,645,852.

In one preferred form of the invention, the antibodies, particularly antibodies to the PEP are immobilized on magnetic beads. This can be accomplished by procedures which are per se known, such as those described in U.S. Pat. Nos. 3,970,518; 4,018,886, 4,855,045 and 4,230,685. In a particular preferred embodiment, attachment of antibodies to magnetic particles is accomplished through a Protein A intermediate. That is, Protein A is first attached to the magnetic particles and the antibodies of choice are then bound to the Protein A. The use of the Protein A intermediate greatly increases the effectiveness of capture by the attached antibodies. (Forsgren et al. (1977) J. Immunol. 99:19) Protein A attaches to the Fc portion of IgG subclass antibodies, thus extending and presenting the Fab portion of these antibodies. The resulting correct orientation of the antibodies and extension away from the particles leads to a very effective interaction between the bound antibodies and their target.

The method of attachment of Protein A to magnetic particles may proceed by any of several processes available through the scientific literature. In one such procedure, magnetic iron oxide particles of approximately 1 micrometer diameter are chemically derivatized by reaction, first with 3-aminopropyltriethoxysilane, then with glutaraldehyde. The derivatized magnetic particles are then mixed with Protein A resulting in a magnetic particle to which Protein A is covalently attached. The antibodies are now added to the Protein A magnetic particles and after a short incubation the protein A-antibody complexes form. (Weetall, H. H. (1976) Meth. in Enzymol. 44:134– 148) These derivatized particles with Protein A-antibodies attached are now ready for use in bacterial cell capture.

GENERAL DESCRIPTION OF THE METHOD OF THE INVENTION—EXAMPLE FOR LISTERIA STRAIN DETECTION

Step 1): As a first step, if the sample (such as food) is not a liquid, the food sample is mixed with liquid, such as water, and blended to liquify. The liquid or liquified food sample is filtered through a course paper, glass or other matrix filter to remove particulates. If an environmental sample, swabs or scrapings of the tested surface are mixed in a collection buffer and then treated as a liquified food sample.

Alternatively, the sample is treated as in the standard FDA or generalized "rapid" immunoassay procedures through the enrichment broth culture step. A standard volume of this culture is then filtered and used in place of the original food or environmental sample.

Step 2): Immobilized antibodies (polyclonal or monoclonal) to target bacterial cells are used to separate Listeria cells from the sample filtrate. In this step, one or more antibodies must be used to recognize all target strains of the genus Listeria. Recognition of other bacteria (i.e., cross-reactivity) can be accepted in this step, as complete specificity is not necessary at this step of the assay.

Figure 4:
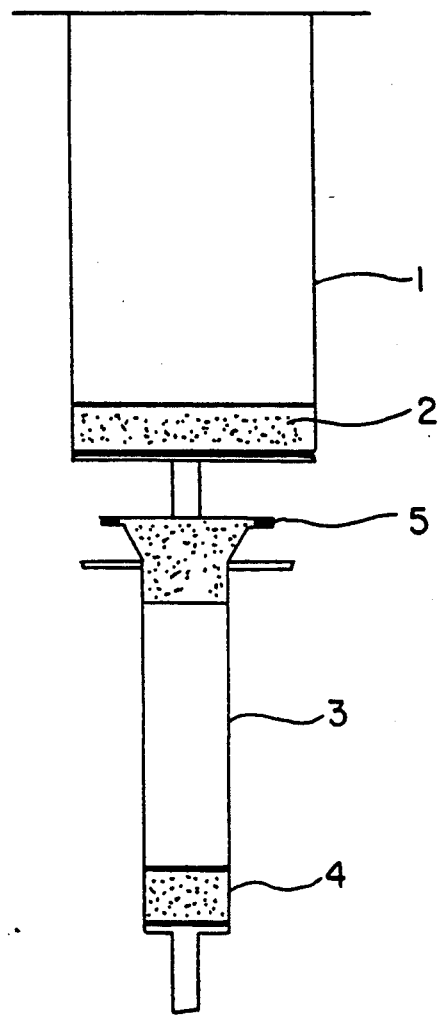
FIG. 4 shows a dual affinity column apparatus for performing the assay.

The antibodies used in step (2) recognize Listeria cell surface antigens, and these antibodies are immobilized on magnetic beads. These antibody coated magnetic beads are added directly to a liquid food sample or filtered liquified sample. After a short incubation step the beads with Listeria cells immobilized thereon, if present in the sample, are separated from the sample matrix by use of a magnetic field. Subsequent washing and immobilization steps are followed by suspension of the Listeria cells immobilized on the magnetic beads, in a small volume of cell lysis solution as described in step (3). Alternatively, polyacrylamide beads coated with Listeria cell surface antibodies are used to immobilize Listeria cells packed into a liquid chromatography column or small syringe barrel. As shown in FIG. 4, the sample filtrate is passed through a column (Column #1) 1 and over the immobilized antibody coated beads 2. The cell surface antibodies capture Listeria cells while the sample filtrate passes through Column #1. After washing the column, the target Listeria cells have been concentrated on Column #1 and separated from the food sample.

Step 3): The immobilized cells are treated by enzymatic means to release target antigens from the cell wall or some other cellular structure. Specifically, immobilized Listeria cells are digested in a small volume (<1 ml) of solution containing a lysis enzyme, such as mutanolysin. The product of this digestion is individual and/or multiple units of cell wall peptidoglycan covalently linked to cell wall teichoic acid. These peptidoglycan-teichoic acid complexes (PEP-TA) are the bacterial target antigens for the immunoassay. A degree of enrichment is achieved in this step as limited bacterial types are digested by mutanolysin. Cells captured but not digested remain whole and immobilized. No potential target antigens are released from these undigested cells.

Step 4): Antibody coated magnetic beads are then separated from the solution (containing the Listeria PEP-TA complexes) with a magnetic field. This solution is removed and applied directly to Column (Column #2) 3. Alternatively, if capture of the Listeria has taken place utilizing Column (Column #1) 1, a second affinity column (Column #2) 3 is then attached to the bottom of (Column #1) (See FIG. 4). Affinity Column #2 contains immobilized monoclonal or polyclonal antibodies to the peptidoglycan moiety of the PEP-TA complex covalently attached to agarose beads 4.

Digested bacterial cell wall components are passed over Column #2 either directly through a slip luer connection 5 between the two columns, or the cell wall digestion solution of Column #1 can be collected and subsequently transferred to Column #2 as is the case when magnetic beads are used. In either case, the free PEP-TA units are captured by immobilized peptidoglycan (PEP) antibodies. A buffer solution is washed through the column to remove all remaining cellular components except the captured PEP-TA complexes.

Step 5): A solution containing monoclonal antibodies to Listeria teichoic acid (TA) is added to Column #2.

These antibodies are specific to Listeria strains. As noted above and shown in FIG. 3, the structure of TA varies among the strains of Listeria and, thus, more than one antibody is required for detection of the entire Listeria genus. On the other hand, if any selected strains are to be identified, the antibodies to any of these strains can be used. These antibodies are labeled directly, or indirectly with detector molecules.

After passing this solution over Column #2 the column is washed thoroughly to remove all labeled antibody not specifically attached to the TA moiety of the PEP-TA complex.

Final specificity of the test is accomplished at this step of the procedure.

Step 6): A small volume of a releasing solution is passed over Column #2 to release the detector molecules attached to the TA antibodies, or labeled TA antibodies.

Step 7): The releasing solution containing the released detector molecules is collected and the amount of label is measured. This measurement can either be a direct indicator of the presence of Listeria strains or can be compared against a set of control columns.

Figure 5:
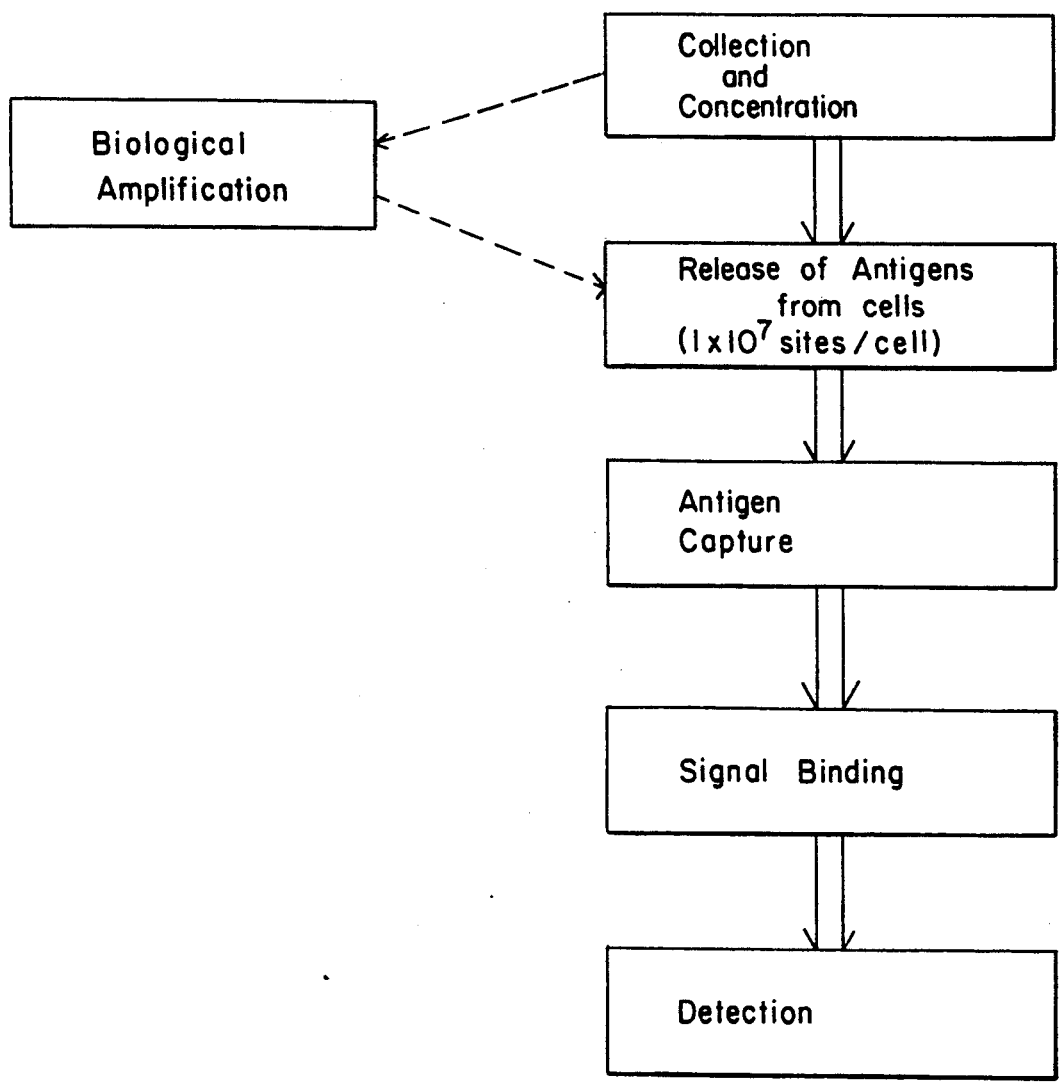
FIG. 5 is a flow chart summarizing the detection method.

These steps are schematically summarized in FIG. 5.

According to the above procedure, all of the target listeriae cells from a given food sample are potentially captured by the magnetic beads or on Column #1. All of the target antigens released from these cells are then potentially captured on Column #2. Finally all of the (TA) from the original captured cells (representing all of the cells in the food sample) become targets for signal antibodies. In other prior art methods, such as both the standard FDA and the new "rapid" immunoassay methods, only a small fraction of the original sample, and therefore a small fraction of the Listeria cells from the sample, is used in the assay. These prior tests may use 1/25,000 to 1/5000 of the original sample and cells. Thus, these methods rely upon growth of the cells at each stage to rebuild the cell number for the final cell identification or immunoassay. The present invention immediately concentrates the bacteria in the original food sample, potentially capturing all of the target cells in the sample, and therefore does not rely upon extended incubation for increasing cell number. Also, because no incubation or dilution steps are involved, under conditions whereby the detection system used is a direct label system or system with a known signal amplification, the observed detection level can be related to a quantitative number of Listeria cells in the original sample. This only applies to objectives of the invention not requiring incubation of the sample.

U.S. Pat. No. 4,556,769 noted above describes an assay method using monoclonal antibodies to peptidoglycan. However, the present invention importantly uses as the final detection step the use of labeled antibodies against teichoic acid. Since there are approximately 30 ribitol units per (TA) molecule, and between an equal number and four times the number of (PEP) disaccharide-peptide repeating units as (TA) molecules in each listeriae cell, the assay of the invention permits targeting of about 8 to 30 times as many antigenic sites, thereby enhancing assay sensitivity. Using the (TA) moiety of the PEP-TA complex as the labeled antibodies target also allows for Listeria strain identification, and thus pathogenic vs. nonpathogenic Listeria. This would not be possible if (PEP) alone were used to assay for Listeria strains. In fact Listeria strain identification is not possible if only cell wall (PEP) is used for a target as other gram positive and most gram negative bacteria share the same (PEP) chemical structure as Listeria (Schleifer, K. H. and Kandler, O., (1972) *Bacteriological Reviews*, 36, p. 404–477). Therefore, the antigenic epitopes are essentially the same.

Other prior art methods also rely upon an incubation step for selective growth of the listeriae or other target bacteria from a background of competing microorganisms. The present invention eliminates competing mcroorganisms by a series of cell separation and specific cell lysis steps.

Prior art methods requiring culturing can only detect viable cells able to reproduce during the incubation steps. Enough cells must recover and reproduce to overcome the cell dilution factor described above and increase the cell number to a level detectable by the assay. The present method is able to detect both viable and nonviable cells. To determine if a Listeria positive food or environmental sample contains viable or nonviable cells parallel tests are conducted. In the first test the sample is processed as described above without a short ($<6$ hr.) incubation step. In the second test an equal amount of filtered sample, from the same original sample, is processed to capture the Listeria cells and washed as described above. A small volume of growth medium is added to the separated magnetic beads or added directly to column #1 and the cells are then incubated. The remainder of the assay procedure as described above is then followed. A statistically significant increase in the detected target antigen level will indicate that viable cells were present in the original sample. Alternatively, if the one step enrichment culture step is used, after making the sample dilution into enrichment broth a standard volume of this broth sample mixture is immediately processed through the assay. After incubation an equal volume of broth sample mixture again is processed through the assay. A comparison of label signals, before and after incubation, is an indication of the presence of viable Listeria or other target bacteria.

As noted above, the assay of the present invention importantly avoids the use of a time consuming bacterial culturing step. However, if the needed sensitivity of the test is not achieved without culturing the Listeria cells, or if cell viability is to be tested, a short incubation of the cells while attached to Column #1 or after separation and concentration using antibody coated magnetic beads can be carried out after step (2) described above. This culturing, however, should be understood as distinguishable from other prior art incubation procedures. Prior procedures involved standard cell culturing in, for example, containers with bacterial broth. A culturing process according to the present invention, on the other hand, cultures and grows the cells as they are attached to a solid matrix via an appropriate antibody. Culturing according to this procedure, more quickly enhances the number of target cells to be identified, because potential competing bacteria have been removed from the column.

To demonstrate the possibility of growing Listeria cells in this manner, cells (strain 1/2a), radioactively labeled with $^{32}P$, are cultured overnight at 37° C. to a cell density of approximately $1 \times 10^8$ cells per ml. Subsequently $1 \times 10^7$ cells are passed over a column containing 0.2 ml bed volume of agarose beads with wheat germ lectin attached. Wheat germ lectins bind to bacterial cell surface sugars. Although inefficient at capturing the Listeria cells, approximately 10%, or $1 \times 10^6$ cells, are captured by the agarose immobilized lectins. After washing the column with Tris-HCl pH 6.4 plus 10 mM NaCl, 1 ml of brain-heart infusion medium is added to the column and with positive pressure forced to enter and surround the agarose beads. Approximately 0.1 ml of liquid is allowed to drop from the column. This liquid is counted for $^{32}P$ and found to contain very few cells.

The column is then capped at the bottom and top and is placed in a 37° C. incubator. After approximately 10 hours incubation the medium is pushed through the column and collected along with 1 ml of fresh medium as a wash. The optical density as a measure of this collected material is determined. The result is an increase in listeriae cells to approximately $1 \times 10^8$ cells. This is a 100 fold increase. Microscopic examination of the cells reveals the vast majority to be characteristic of Listeria strains.

In the above described procedure, particularly at step (7), antibodies directed against listeria (TA) serve as the signal or detector antibodies. These are labeled either directly or indirectly with labels used in other known immunoassays. Direct labels (labels attached directly to the anti (TA) antibodies) may include fluorgenic, chemiluminescdent, bioluminescent, radioactive, metallic, biotin or enzymatic molecules. Methods of combining these labels to antibodies are well known to those in the art. Examples include the method of Hijmans, W. et al. (1969), Clin. Exp. Immunol. 4, 457-, for fluorescein isothiocyanate, the method of Goding, J. W. (1976), J. Immunol. Meth. 13, 215- for tetramethylrhodamine isothiocyanate, and the method of Engrall, E. (1980), Meth. in Enzymol. 70, 419–439 for enzymes.

These (TA) detector antibodies may also be labeled indirectly. In this case the actual detection molecule as described above is attached to a secondary antibody or other molecule with binding affinity for the anti (TA) detector antibody. If a secondary labeled antibody is used it is preferably a general antibody to a class of antibody from the animal species used to raise the (TA) monoclonal antibodies. In this case the immobilized antibody to (PEP) would of necessity be raised in another animal host or be of a different antibody class or fraction of the same class of antibody. Another example of indirect labeling is covalent coupling of biotin to the (TA) monoclonal antibodies. Subsequent addition of avidin-biotin conjugates produced by the method of Bayer, E. A. (1979), Meth. in Enzymol. 62, 308-, or strepavidin-biotin conjugates, where the biotin is labeled, and binding of these conjugates to the (TA) antibody-biotin complex provides the detection label.

Release of the label from Column #2 may be achieved by the use of an organic solvent (such as methanol or acetone), or an aqueous solution containing an agent to disrupt the binding of the label, or any part of the connection between the immobilizing agent and the label. Organic-aqueous mixtures may also be used. Aqueous agents may include solutions of high or low pH, inorganic salts, detergents such as sodium lauryl sulfate, and chaotropic agents such as guanine or urea.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method for the detection of Listeria strains which comprises:
   a) combining a sample potentially containing Listeria strains with a solid support having immobilized thereon antibodies to listeriae cells, to thereby obtain captured listeriae cells from said sample;
   b) treating said captured listeriae cells to release peptidoglycan-teichoic acid, PEP-TA, complexes from said listeriae cells;
   c) combining said PEP-TA complexes with antibodies specific for peptidoglycan, to thereby obtain captured PEP-TA complexes;
   d) combining said captured PEP-TA complexes with labeled antibodies to teichoic acid, to thereby bind said labeled antibodies to said captured PEP-TA complexes;
   e) treating the thus produced PEP-TA labeled antibody complex to release the label from said PEP-TA-labeled antibody complex; and
   f) measuring said label to detect or measure the presence of Listeria strains in the sample.

2. The method according to claim 1, wherein growth medium is added to said captured listeriae cells and said cells are incubated prior to step b).

3. The method according to claim 1, wherein said treatment of said captured listeriae cells is performed with lytic enzymes.

4. The method of claim 3, wherein said lytic enzyme is mutanolysin.

5. The method according to claim 1, wherein said antibodies to teichoic acid are specific to teichoic acid found in pathogenic Listeria strains.

6. The method according to claim 1, wherein said antibodies to said listeriae cells and said antibodies specific to peptidoglycan are polyclonal antibodies.

7. The method according to claim 6, wherein said antibodies to teichoic acid are monoclonal antibodies.

8. The method according to claim 1, wherein said antibodies to listeriae cells are immobilized on solid beads.

9. The method according to claim 1, wherein said antibodies are immobilized on a matrix selected from the group consisting of magnetic beads, polyacrylamide beads, agarose beads, polysaccharides, cross-linked dextrans, glass beads, latex beads, glass fiber filters, cellulose nitrate filters and nylon filters.

10. The method according to claim 1, wherein said labeled antibodies are labeled with fluorogenic, chemiluminescent, bioluminescent, radioactive, metallic, biotin or enzymatic molecules.

11. The method according to claim 1, wherein said labeled antibodies are labeled with an antibody having affinity to said antibodies to teichoic acid.

12. The method according to claim 5, wherein said antibodies to teichoic acid are specific to teichoic acid found in pathogenic Listeria strains SV 1/2a and 4b.

13. A method for the detection of Listeria strains which comprises:
   a) combining a sample with a solid support having immobilized thereon antibodies to listeriae cells, to thereby obtained captured listeriae cells from said sample;
   b) treating said captured listeriae cells with lytic enzymes to lyse said listeriae cells and release peptidoglycan-teichoic acid, PEP-TA, complexes;
   c) passing said PEP-TA complexes through an affinity column containing an affinity matrix having bound thereto antibodies to peptidoglycan, to thereby obtain captured PEP-TA complexes on said matrix;
d) passing a solution containing labeled antibody to teichoic acid through said column, whereby said labeled antibodies bind to said captured PEP-TA complexes;
e) eluting said column with a releasing agent to release said labeled antibody;
f) collecting said labeled antibody; and
g) measuring the label of said labeled antibody to detect or measure the presence of Listeria strains in said sample.

14. The method according to claim 13, wherein said lytic enzyme is mutanolysin.

15. The method according to claim 13, wherein said antibodies to said listeriae cells and said antibodies specific to peptidoglycan are polyclonal antibodies and said antibodies to teichoic acid are monoclonal antibodies.

16. The method according to claim 15, wherein said monoclonal antibodies to teichoic acid are specific to teichoic acid found in pathogenic Listeria strains.

17. The method according to claim 16, wherein said antibodies to teichoic acid are specific to teichoic acid found in pathogenic Listeria strains SV 1/2 a and 4b.

18. A method for the detection of Listeria strains which comprises:
a) combining a sample with a solid support having immobilized thereon polyclonal antibodies to listeriae cells, to thereby obtain captured listeriae cells from said sample;
b) treating said captured listeriae cells with mutanolysin to lyse said listeriae cells and release peptidoglycan-teichoic acid, PEP-TA, complexes;
c) passing said PEP-TA complexes through an affinity column containing an affinity matrix having bound thereto polyclonal antibodies to peptidoglycan, to thereby obtain captured PEP-TA complexes on said matrix;
d) passing a solution containing labeled monoclonal antibody to teichoic acid through said column, whereby said labeled antibodies bind to said captured PEP-TA complexes;
e) eluting said column with a releasing agent to release said labeled antibody;
f) collecting said labeled antibody; and
g) determining the label of said labeled antibody to detect or measure the presence of Listeria strains in said sample.

19. The method according to claim 18, wherein said antibodies to teichoic acid are specific to teichoic acid found in pathogenic Listeria strains SV 1/2a and 4b.

20. A method for the detection of Listeria strains which comprises:
a) combining a sample potentially containing Listeria strains with a magnetic solid support having immobilized thereon first antibodies to listeriae cells, to thereby obtain captured listeriae cells from said sample;
b) exposing to a magnetic field said magnetic support having bound thereto said first antibodies and captured listeriae cells to separate said magnetic support from said sample;
c) suspending said magnetic support having bound thereto captured listeriae cells in a cell lysis solution to release peptidoglycan-teichoic acid, PEP-TA, complexes from said listeriae cells;
d) separating said magnetic support from said PEP-TA complexes by exposure to a magnetic field;
e) combining said, PEP-TA, complexes with second antibodies specific for peptidoglycan, to thereby obtain captured PEP-TA complexes;
f) combining said captured PEP-TA complexes with labeled antibodies to teichoic acid, to thereby bind said labeled antibodies to said captured PEP-TA complexes;
g) treating the thus produced PEP-TA-labeled antibody complex to release the label from said PEP-TA-labeled antibody complex; and
h) measuring said label to detect or measure the presence of Listeria strains in the sample.

21. The method according to claim 20, wherein said first antibodies are bound to said magnetic support through Protein A.

22. A method for the detection of Listeria strains which comprises:
a) combining a sample with magnetic beads having immobilized thereon first antibodies to listeriae cells, to thereby obtained captured listeriae cells from said sample;
b) exposing to a magnetic field said magnetic beads having bound thereto said first antibodies and captured listeriae cells to separate said magnetic beads from said sample;
c) suspending said magnetic beads having bound thereto captured listeriae cells with lytic enzymes to lyse said listeriae cells and release peptidoglycan-teichoic acid, PEP-TA, complexes;
d) separating said magnetic beads by exposure to a magnetic field to provide a solution containing said PEP-TA complexes;
e) passing said solution containing PEP-TA complexes through an affinity column containing an affinity matrix having bound thereto antibodies to peptidoglycan, to thereby obtain captured PEP-TA complexes on said matrix;
f) passing a solution containing labeled antibody to teichoic acid through said column, whereby said labeled antibodies bind to said captured PEP-TA complexes;
g) eluting said column with a releasing agent to release said labeled antibody;
h) collecting said labeled antibody; and
i) measuring the label of said labeled antibody to detect or measure the presence of Listeria strains in said sample.

23. The method according to claim 22, wherein said lytic enzyme is mutanolysin.

24. The method according to claim 22, wherein said antibodies to said listeriae cells and said antibodies specific to peptidoglycan are polyclonal antibodies and said antibodies to teichoic acid are monoclonal antibodies.

25. The method according to claim 24, wherein said first antibodies are bound to said magnetic beads through Protein A.

* * * * *